United States Patent [19]

Fahmy et al.

[11] Patent Number: 4,855,474

[45] Date of Patent: Aug. 8, 1989

[54] PROCESS FOR PRODUCTION OF PHOSPHOROTHIOIC DICHLORIDES

[75] Inventors: Mohamed H. Fahmy, Wilmington; James R. Sanborn, Newark, both of Del.

[73] Assignee: E. I. Du Pont De Nemours and Company, Wilmington, Del.

[21] Appl. No.: 27,234

[22] Filed: Mar. 18, 1987

[51] Int. Cl.$^4$ .............................................. C07F 9/14
[52] U.S. Cl. ...................................... 558/95; 558/202
[58] Field of Search ................................. 558/95, 202

[56] References Cited

FOREIGN PATENT DOCUMENTS 160344 11/1985 European Pat. Off. .
1161556 1/1964 Fed. Rep. of Germany .
123096 11/1976 German Democratic Rep. .
1338857 11/1973 United Kingdom .

OTHER PUBLICATIONS

M. Schnell, G. Erfurt, and H. Zinner, *Journal Prakt. Chemie*, 319, pp. 723–726 (1977); translation attached.
Kosolapoff and Maier, *Organic Phosphorus Cpds*, 7, p. 504, (1976), attached translation.

*Primary Examiner*—Anton H. Sutto

[57] ABSTRACT

The aldehyde RCHO is reacted with $PCl_3$ and sulfur monochloride in the presence of chloride ion and under anhydrous conditions to give $RCHClO(S)PCl_2$.

9 Claims, No Drawings

PROCESS FOR PRODUCTION OF PHOSPHOROTHIOIC DICHLORIDES

BACKGROUND OF THE INVENTION

This invention relates to a process for producing phosphorothioic dichlorides from aldehyde, $PCl_3$, and sulfur monochloride reactants.

The following process is disclosed in EPO patent application No. 160,344 published Oct. 6, 1985:

$$CCl_3CHO + PCl_5 \rightarrow CCl_3CHClOPCl_4$$

$$CCl_3CHClOPCl_4 + H_2S \rightarrow CCl_3CHClO(S)PCl_2$$

the sequence of reactions being expressed in terms of desired intermediate and final reaction products only. The same general process is disclosed in East German Pat. No. 123,096 granted Nov. 20, 1976 except that a broader range of aldehydes than chloral ($CCl_3CHO$) are used. V. M. Schnell, G. Erfurt, and H. Zinner, *J. Prakt. Chemie*, 319 (1977) pp. 723–726 also discloses the reaction as follows:

$$RCHO + PCl_5 \longrightarrow RCHClOPCl_4 \xrightarrow{H_2S} RCHClO\overset{S}{\underset{\|}{P}}Cl_2$$

wherein R is polyhaloalkyl, disclosing in particular $CCl_3$ and $CHCl_2$. One disadvantage of the process disclosed in these publications is the use of $H_2S$ as a sulfurizing agent, the disadvantage arising from the extreme toxicity of $H_2S$, requiring extreme care in transportation, if necessary, and handling. Another disadvantage arises from the need to use $PCl_5$ which as a solid usually requires the use of elevated temperatures in order to keep this reactant in solution.

G. Schrader discloses in German Patent 1161556 (1964) and in *Organic Phosphorus Compounds*, 7 (1976), edited by G. Kosolapoff and L. Maier, on page 504, the use of sulfur monochloride as a sulfurizing agent in the following reaction:

$$3\text{s-BuOPCl}_2 + S_2Cl_2 \rightarrow 2\text{s-BuOP(S)Cl}_2 + P(O)Cl_3 + \text{s-BuCl}$$

SUMMARY OF THE INVENTION

The present invention provides an improved process for preparing phosphorothioic dichlorides, the process comprising contacting and reacting a compound of the formula RCHO, wherein R is an alkyl or haloalkyl moiety which is inert under the reaction conditions, with $PCl_3$ and sulfur monochloride in the presence of a catalytic amount of chloride ion in the liquid phase and under anhydrous conditions, and obtaining as a result thereof compound of the formula $RCHClOP(S)Cl_2$.

In its simplest form, the process can be represented by the following equation:

$$RCHO + PCl_3 + S_2Cl_2 \xrightarrow{Cl^-} RCHClOP(S)Cl_2$$

wherein R has the same meaning as above. Sulfur monochloride is a safer sulfurizing agent than $H_2S$.

DESCRIPTION OF THE INVENTION

The process of the invention can be conducted at atmospheric pressure but is preferably conducted under $N_2$ blanket to exclude the presence of moisture so as to lessen the possibility for unwanted side reactions.

The process should be conducted in a reactor which presents a surface to the reaction which is inert to the reaction under the conditions of operation. Inert materials for reactor lining or reactor construction include glass and any of the metals normally inactive, e.g., stainless steel.

The order of addition of the reactants to the reaction zone within the reactor is not critical, in that all of the three reactants can be added simultaneously and all three reactants can be present in the reaction zone at the same time. In one embodiment, however, $PCl_3$ and sulfur monochloride are added first to the reaction zone, followed by gradual addition of the compound RCHO to the reaction zone to lessen the rate of heat evolution caused by the reaction. There is no need to withhold the sulfurizing agent while the other reactants react as in the sequential reactions disclosed in prior publications described in the Background of the Invention.

Generally, the reaction should be carried out at a temperature from $-30°$ to $+40°$ C. Lower temperatures are more difficult to achieve and do not provide any advantage. Higher temperatures can lead to unwanted side-reactions which can lessen the yield of the desired phosphorothioic dichloride. A preferred temperature range is from $-20°$ to $+25°$ C.

The $PCl_3$ reactant provides the liquid phase within which the reaction occurs, the other reactants being soluble in $PCl_3$. The $PCl_3$ and sulfur monochloride reactants are added to the reaction zone in amounts which are at least equimolar to the RCHO reactant. Excess $PCl_3$ and sulfur monochloride may be used.

When the amount of $PCl_3$ used does not provide the amount of liquid phase desired in the reaction zone, then additional organic solvent for the reactants, which are inert to the reaction can be present. Typically, the organic solvent will be one which is aprotic. Examples of such solvents include dichloromethane, chloroform, carbon tetrachloride, toluene, and benzene. To aid in the reaction, the liquid phase is stirred while the reaction is occurring. Preferably, the solvent selected will also be solvent for the phosphorothioic dichloride reaction product.

The reaction should be carried out under anhydrous conditions, i.e., water should be excluded from the reactor and the reactants in the process, so as to minimize unwanted side-reactions.

The R group of the RCHO reactant can be any alkyl or haloalkyl moiety that is inert to the reaction. Thus, the R group is unchanged by the reaction and has the same identity in the phosphorothioic dichloride reaction product. Examples of R groups include $C_1$ to $C_6$ alkyl and $C_1$ to $C_6$ haloalkyl. Surprisingly, the carbon atom in the RCHO reactant is monochlorinated to become RCHClO— in the reaction product, and is not dichlorinated as disclosed in the aldehyde/$PCl_5$ reaction disclosed in Nikolenco and Popov, *J. Gen. Chem.*, USSR 32, 29 (1962) wherein HCl is a resultant by-product. The simplest R group is $CCl_3$ whereby the reactant is $CCl_3CHO$ commonly known as chloral. Examples of additional specific R groups include $C(CH_3)_3—$, $CHCl_2—$, $CH_3CH_2—$.

The sulfur monochloride reactant provides the reactive group SCl but this reactant is normally provided to the reaction as the dimer $S_2Cl_2$, which can also be represented as ClSSCl. Included within the term sulfur monochloride is the aforesaid dimer wherein the chloride and sulfur atoms are present in stoichiometric proportions and in addition wherein excess sulfur may be present, which may be represented by the formula $ClS(S_n)SCl$, $S_n$ representing the stoichiometric excess.

The chloride ion catalyst can be provided by a chloride-containing compound such as quaternary ammonium chloride, quaternary phosphonium chloride, quaternary sulfonium chloride, and cyclic or acylic polyethyleneoxy ether chloride salt complex or a mixture thereof. A preferred catalyst compound for economy reasons is benzyltributyl ammonium chloride. The chloride-containing compound need only provide chloride ion to the reaction but is otherwise inert to the reaction.

The resultant phosphorothioic dichloride $(RCHClO(S)PCl_2)$ has insecticidal properties and may be used as an intermediate to make other insecticides by reaction with alcohol, phenol, thiophenol, or mercaptan as disclosed in East German Pat. Nos. 107,581 and 123,096.

Preferably, the phosphorothioic dichloride reaction product of the process has the identity $CCl_3CHClO(S)PCl_2$ and this is further reacted with ethanol to make O,O-diethyl-O-(1,2,2,2-tetrachloroethyl)phosphorothioate as described in EPO patent publication No. 160,344.

EXAMPLES

Examples of the process of the present invention, in which parts are by weight and temperatures are give in degrees centigrade unless otherwise indicated, are presented hereinafter.

EXAMPLE 1

To a 100 ml, 3-neck glass flask fitted with a stirrer and $N_2$ blanket, were added 23.6 g (0.17 mole) of $PCl_3$, 8.1 g (0.06 mole) of sulfur monochloride and the flask was cooled to $-5°$. To the flask was then added 0.47 g (0.0015 mole) of benzyltributyl ammonium chloride and dropwise over a period of about two minutes, 4.48 g (0.03 mole) of chloral which had been previously distilled over $H_2SO_4$. The reaction mixture was stirred at $-5°$ C. for about 5-6 hours and then diluted with hexane. The resultant solution was filtered and concentrated under vacuum and the liquid residue was again diluted with hexane and filtered, and the filtrate was concentrated under vacuum to yield a yellow liquid. This liquid was distilled in a Kugelrohr apparatus (75° C., 0.03 mm) yielding a yellow liquid which was predominantly $CCl_3CHClO(S)PCl_2$ as confirmed by NMR and GC-MS data. NMR ($CDCl_3$), $\delta$ 6.65 (d, 1H, J=14).

EXAMPLE 2

To a solution stirred under nitrogen at $-10°$ C. of 170 ml 2 molar $PCl_3$ in $CH_2Cl_2$ was added 1.8 g (0.006 mole) of benzyltributyl ammonium chloride and 15.68 g (0.116 mole) of sulfur monochloride. To this reaction medium was added dropwise over a period of about one minute 5 g (0.058 mole) of pivaldehyde. Stirring of the reaction mixture was continued at $-5°$ C. for about 18 hours. The resultant solutions was concentrated under vacuum and the liquid residue was diluted with hexane and filtered. The filtrate was concentrated under vacuum and the resultant residue was distilled in a Kugelrohr apparatus (50° C., 0.3 mm Hg) to give a yellow oil having the formula $C(CH_3)_3CHClO(S)PCl_2$ as confirmed by NMR spectral data. NMR ($CDCl_3$), $\delta$ 6.12 (d, 1H, J=14), 1.10 (s, 9H).

EXAMPLE 3

A 1 liter 3-neck flask equipped with a mechanical stirrer, addition funnel, thermometer and $N_2$ inlet was charged with 250 ml of 2.0 molar $PCl_3$ in $CH_2Cl_2$ (0.5 mol of $PCl_3$), 23.2 g (0.17 mol) of sulfur monochloride, and 2.69 g (0.0086 mole) of benzyltributyl ammonium chloride. This mixture was cooled to $-5°$ C. and 5 g of propionaldehyde (0.086 mol) was added dropwise over a period of about one minute. The resulting solution was stirred at $-10°$ C. overnight and then concentrated under vacuum, diluted with hexane and filtered. The filtrate was concentrated and distilled in a Kugelrohr apparatus (0.15 mm Hg) to give a yellow liquid shown by NMR to be the desired compound $CH_3CH_2CHClO(S)PCl_2$. NMR ($CDCl_3$), $\delta$ 6.35 (dt, 1H, J=14, J=5), 2.18 (m, 2H), 1.12 (t, 3H, J=7) b.p. 75°–80° C.

As many widely different embodiments of the process of this invention may be made without departing from the spirit and scope thereof, it is to be understood that this invention is not limited to these Examples except as may be defined in the appended claims.

What is claimed:

1. A process comprising contacting and reacting a compound of the formula RCHO, wherein R is an alkyl or haloalkyl moiety which is inert under the reaction conditions, with $PCl_3$ and sulfur monochloride in the presence of a catalytic amount of chloride ion in the liquid phase and under anhydrous conditions and obtaining as a result thereof compound of the formula $RCHClOP(S)Cl_2$, said chloride ion being provided by at least one compound selected from the group consisting of quaternary ammonium, phosphonium, or sulfonium chlorides and polyethyleneoxy ether chloride salt complex.

2. The process of claim 1 wherein the amounts of $PCl_3$ and sulfur monochloride are at least equimolar with respect to the amount of compound of the formula RCHO present.

3. The process of claim 1 wherein the reaction temperature is from $-30°$ to 40° C.

4. The process of claim 1 wherein the amount of chloride ion present is from 0.1 to 5 mole % of the amount of compound of the formula RCHO present.

5. The process of claim 1 wherein the compound of the formula RCHO is gradually added to the liquid phase containing the remaining reactants and catalyst.

6. The process of claim 1 wherein the liquid phase is provided by the $PCl_3$ reactant.

7. The process of claim 6 wherein additional organic solvent for the reactants is present, said solvent being inert to the reaction.

8. The process of claim 1 where R is $CCl_3$.

9. The process of claim 1 wherein the compound providing the chloride ion is benzyltributyl ammonium chloride and the reaction temperature is $-5°$ to $-10°$ C.

* * * * *